United States Patent [19]
Kumar

[11] Patent Number: 6,046,960
[45] Date of Patent: Apr. 4, 2000

[54] APPARATUS AND METHOD FOR DISCRIMINATING TRUE AND FALSE ULTRASONIC ECHOES

[75] Inventor: Lalit Kumar, Shelburne, Vt.

[73] Assignee: Simmonds Precision Products, Inc., Charlotte, N.C.

[21] Appl. No.: 08/121,849

[22] Filed: Sep. 16, 1993

[51] Int. Cl.[7] .......................... G01S 15/00; G01F 23/296
[52] U.S. Cl. .......................... 367/87; 367/908; 73/290 V
[58] Field of Search .............................. 367/87, 97, 908, 367/99; 73/290 V

[56] References Cited

U.S. PATENT DOCUMENTS

| | | | |
|---|---|---|---|
| H608 | 3/1989 | Goolsby | 367/89 |
| 4,000,650 | 1/1977 | Snyder | 73/290 V |
| 4,596,144 | 6/1986 | Panton et al. | |
| 4,727,277 | 2/1988 | Adams | 310/321 |
| 4,955,004 | 9/1990 | Viscovich | 367/137 |
| 4,992,998 | 2/1991 | Woodward | 367/99 |
| 5,150,334 | 9/1992 | Crosby | 367/98 |
| 5,157,639 | 10/1992 | Leszczynski | 367/99 |

FOREIGN PATENT DOCUMENTS

| | | |
|---|---|---|
| 0262990A2 | 4/1988 | European Pat. Off. . |
| 0337293A1 | 10/1989 | European Pat. Off. . |
| 0429687A1 | 6/1991 | European Pat. Off. . |
| 3337690A1 | 4/1985 | Germany . |
| 2230608A | 10/1990 | United Kingdom . |

*Primary Examiner*—Ian J. Lobo
*Attorney, Agent, or Firm*—Richard A. Romanchik; William E. Zitelli; Leonard L. Lewis

[57] ABSTRACT

Apparatus for discriminating true echoes from false echoes in an ultrasonic liquid gauging system, comprising: means for producing electrical representations of an echo sequence received after an ultrasonic transmission, wherein the echo sequence contains one or more returned echoes that may be a true or false echo; and means for determining returned echo energy, wherein echo energy is a factor used to distinguish a true echo from a false echo.

20 Claims, 7 Drawing Sheets

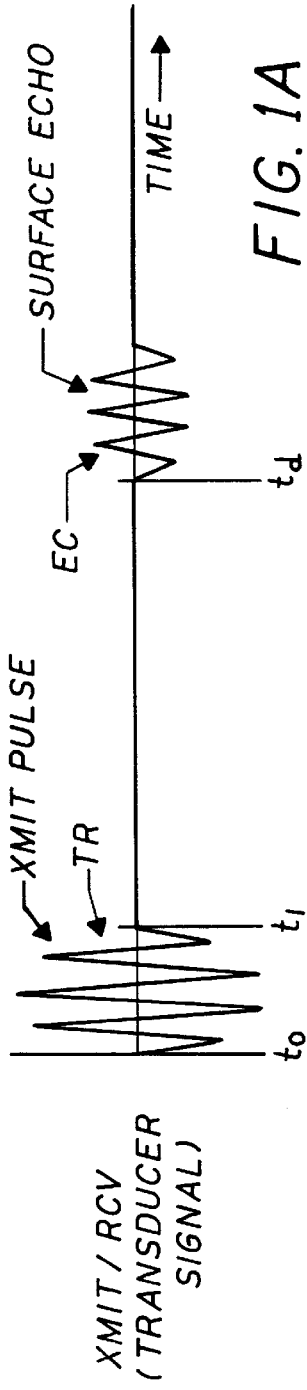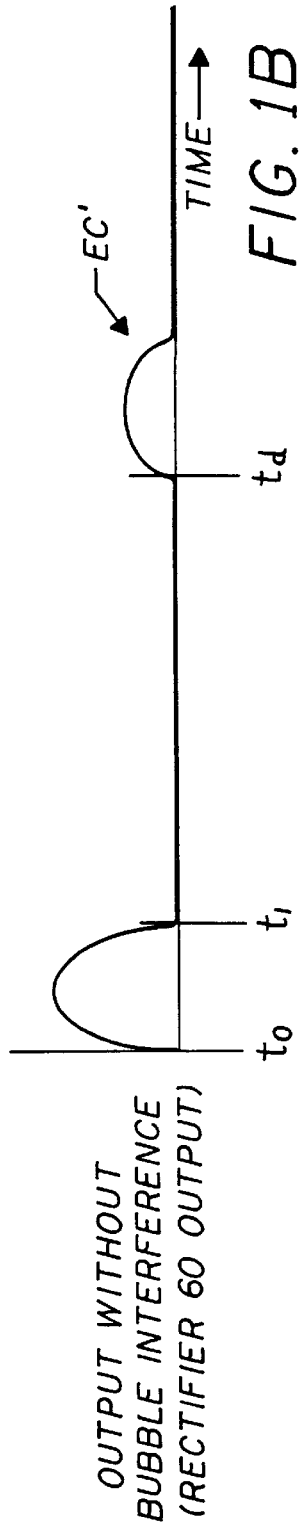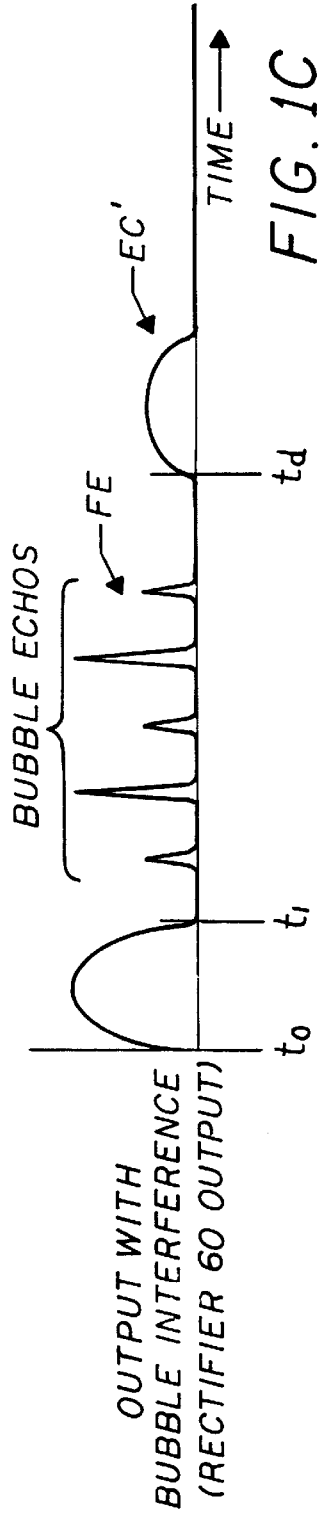

ns and methods for discriminating true and false echoes to improve accuracy of such systems.

APPARATUS AND METHOD FOR DISCRIMINATING TRUE AND FALSE ULTRASONIC ECHOES

BACKGROUND OF THE INVENTION

The invention relates generally to liquid gauging systems of the type that use ultrasonic echo ranging to determine liquid levels. More particularly, the invention relates to methods and apparatus for discriminating true and false echoes to improve accuracy of such systems.

It is well known to use ultrasonic echo ranging to determine liquid levels. Common applications include fuel gauging systems in fuel tanks. Typically, one or more ultrasonic transducers are disposed near the bottom of a liquid tank or container. The transducers emit ultrasonic pulses on the order of 1 megahertz frequency towards the liquid surface. Each ultrasonic pulse is reflected at the fuel/air interface and returns in the form of an echo pulse. The echo pulses are then detected by the same transducer that transmitted the pulse or are detected by a different sensor. The detection sensor typically produces an electrical output signal that corresponds to receipt of the echo. Thus, the round trip time from pulse emission to echo detection corresponds to the distance of the liquid surface from the sensors. Characterization data of the fuel tank can thus be used with the level detection data to determine liquid quantity in the tank.

Ultrasonic liquid level detection in fuel tanks such as are used on aircraft is complicated by several factors. First, water tends to accumulate in the bottom of the fuel tanks, particularly on aircraft that fly at higher altitudes over extended distances, such as, for example, transoceanic commercial flights. Water at the bottom of the tank can present a fuel/water interface that reflects ultrasonic energy in the form of false echoes back to the transducers when such transducers are disposed at or near the tank bottom. Such false echoes can be mistaken for true fuel level echoes and thus give a false indication of fuel level and quantity.

Another problem that arises in fuel tanks is the presence of air bubbles. Aircraft manufacturers have run tests that indicate the presence of air bubbles, under some conditions large in size and quantity, due to fuel slosh and vibration under various flight scenarios. Air bubbles present a fuel/air interface that can reflect ultrasonic energy in the form of false echoes. These echoes can also be misinterpreted as false liquid level readings.

Accordingly, the objective exists for apparatus and methods for discriminating true and false echoes in ultrasonic liquid level sensing systems. Such apparatus and methods should be capable of distinguishing true echoes from false echoes such as may be caused by air bubbles and other false interfaces.

SUMMARY OF THE INVENTION

In response to the aforementioned objectives, the present invention contemplates a method for discriminating true and false echoes in an ultrasonic liquid gauging system comprising the steps of:

a. transmitting an ultrasonic pulse toward the liquid surface;

b. detecting true and false echoes and converting the echoes into electrical signals after a predetermined delay interval after transmission; and c. identifying a true echo from a false echo based on energy of the echoes.

The invention also contemplates apparatus for carrying out the described method, which in one embodiment is an apparatus for discriminating true echoes from false echoes in an ultrasonic liquid gauging system, comprising: means for producing electrical representations of an echo sequence received after an ultrasonic transmission, wherein the echo sequence contains one or more returned echoes that may be a true or false echo; and means for determining returned echo energy, wherein echo energy is a factor used to distinguish a true echo from a false echo.

These and other aspects and advantages of the present invention will be readily understood and appreciated by those skilled in the art from the following detailed description of the preferred embodiments with the best mode contemplated for practicing the invention in view of the accompanying drawings.

BRIEF DESCRIPTION OF THE DRAWINGS

FIGS. 1A–1C are a series of graphs showing in a simplified manner transmit/receive ultrasonic signals and corresponding echo profiles as typically occur in fuel level sensing applications;

DETAILED DESCRIPTION OF THE INVENTION

Figure 2A:
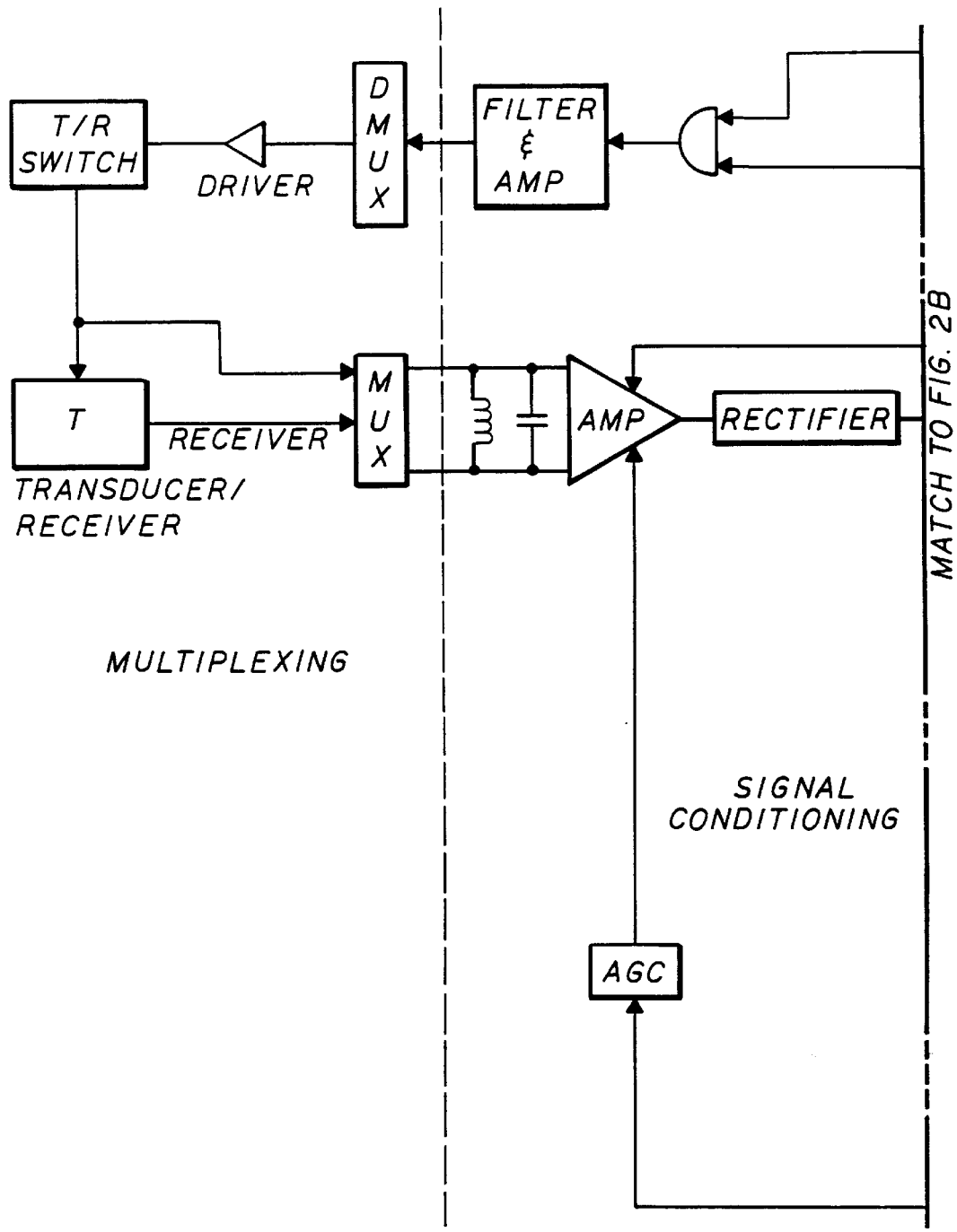
FIGS. 2A, 2B and 2C is a detailed functional block diagram of a fuel gauging system that embodies the teachings of the present invention.

With reference to FIGS. 1A–1C, I show in a simplified representative manner typical signals that occur during ultrasonic liquid level sensing, such as in an aircraft fuel tank. Although the invention is described herein with respect to an ultrasonic fuel level sensing system, those skilled in the art will readily appreciate that the invention can advantageously be used in other ultrasonic echo ranging applications. Furthermore, while the preferred embodiment of the invention is realized in the form of a microprocessor based control system, the invention can also be implemented without a microprocessor controller using digital signal processing techniques well known to those skilled in the art.

In FIG. 1A, the ultrasonic acoustic signatures for a typical transmit and receive pulse pair are shown. The transmit pulse (TR) is assumed to start at time=$t_0$ and may be, for example, a 1 megahertz frequency signal produced by a conventional transducer such as part no. 2-11178 available from Zevex. The transmit pulse is directed towards the liquid surface. After a delay period $t_d$ which represents that time required for the transmitted ultrasonic pulse to reach the surface, be reflected back towards the transducer and be detected by the transducer, the transducer now serves as an ultrasonic receiver and converts the echo, EC, into an amplitude variant analog signal that corresponds to the strength of the received echo.

In practice, of course, the received echo has a somewhat more complicated profile. This does not have an appreciable effect, however, on the usefulness of the present invention. For example, immediately after the transmit period ends at about time $t_1$, a large output signal is produced by the transducer (not shown) because of transducer ringing and close-in reflections. As is well known, this initial echo-like response can be excluded from the valid echo profile by including an appropriate blanking time that disables the signal processing circuits until after time $t_1$.

FIG. 1B illustrates the transmit and receive signal envelopes under conditions in which there is no detected bubble or water/fuel interference. The echo envelope EC' can be produced simply by demodulating the amplitude variant high frequency ultrasonic echo EC into a corresponding amplitude variant low frequency by suitable rectification and filtering of the carrier frequency.

As shown in FIG. 1C, however, the actual echo profile will include spurious noise spikes or false echoes, FE. These false echoes may be caused by air bubbles, for example. If water is at the bottom of a fuel tank such that a fuel/water interface is present between the transducer and the surface fuel/air interface, another false echo will be produced, although such an echo will tend to be less random than air bubbles. The fuel/water echoes will not be fixed, however, because of accumulation of water in the tank, for example. Thus, an actual echo profile for a single transmit/receive cycle will include a number of echoes, one of which is the true echo from the liquid surface and any number of false echoes that may have peak amplitudes comparable to the true echo.

The variable nature of the false echoes due to the dynamic conditions of a fuel tank in an aircraft makes conventional peak amplitude based discrimination of true and false echoes inaccurate and unreliable. Furthermore, conventional pulse width measurement also is unsuitable because the echo envelope of such false echoes is somewhat unpredictable. Time variable threshold detection techniques suffer from the need for repetitive transmissions and also the unpredictability of the true and false echo envelopes.

In accordance with an important aspect of the present invention, true and false echoes in an echo profile are discriminated by determining the relative or actual energy of the received echo signals. Because the echo energy detection technique relies primarily on a determination of the total energy (or substantial portion of the total energy) of the received echoes, the ability to discriminate true and false echoes is less sensitive to the individual echo envelope characteristics.

Although echo energy detection can, if desired, be used each transmit/receive cycle for locating the true echo, I have found that such frequent measurements are not necessary for all applications. In some cases, the energy detection technique can be used to verify that the first echo received after the blanking time (i.e. the second temporal echo received after the transmission period ends) is in fact the true echo. Thus, a simple amplitude based detection scheme can be used each transmit/receive cycle, with the energy based verification technique being used at a less frequent rate, for example every five transmit/receive cycles.

The echo energy detection concept of the present invention is particularly well suited to discriminating false bubble and water/fuel echoes because the amount of energy reflected by the air/fuel interface at the liquid surface is significantly greater than the energy reflected by air bubbles and a water/fuel interface.

Figure 2B:
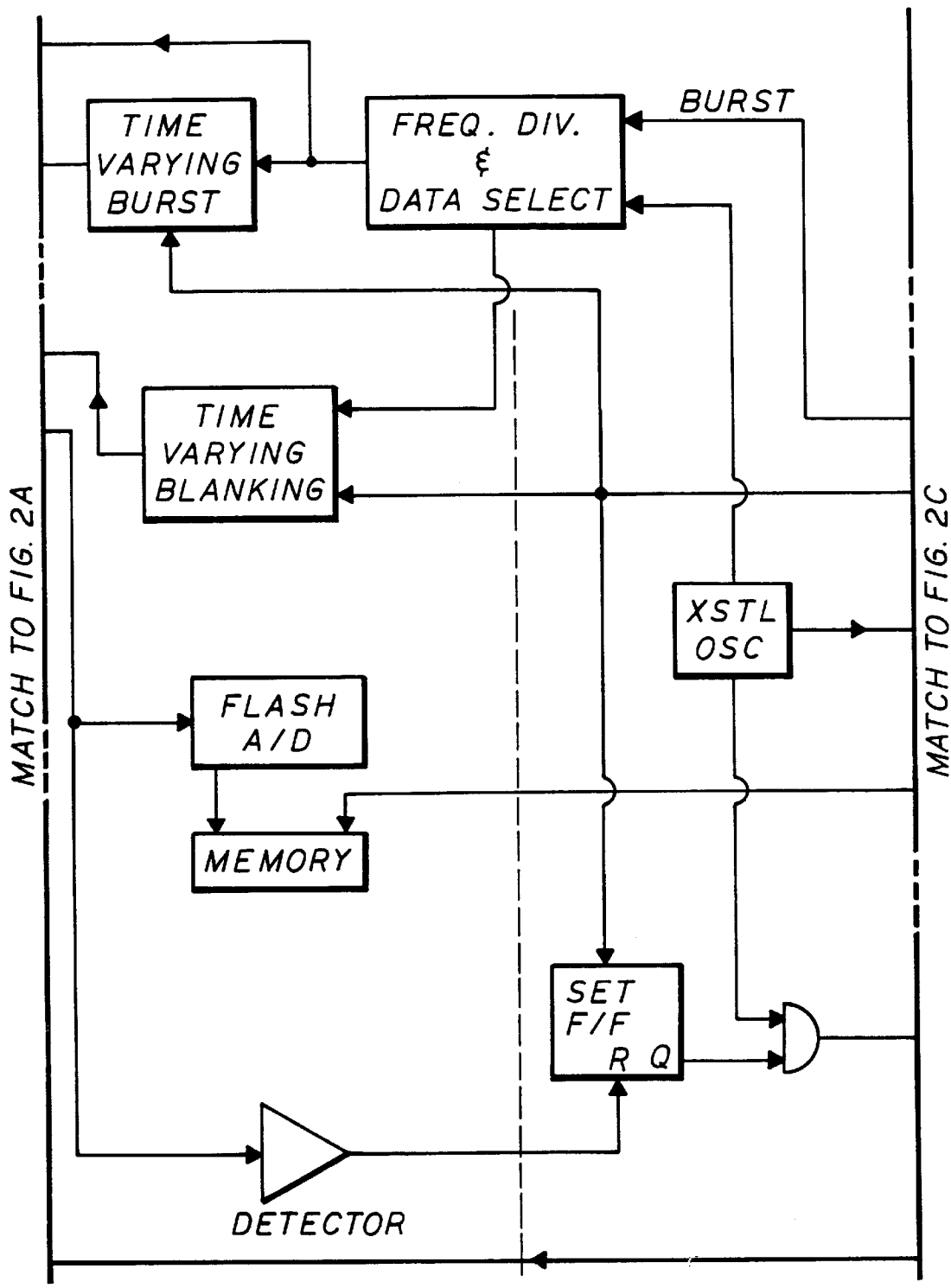
Figure 2C:
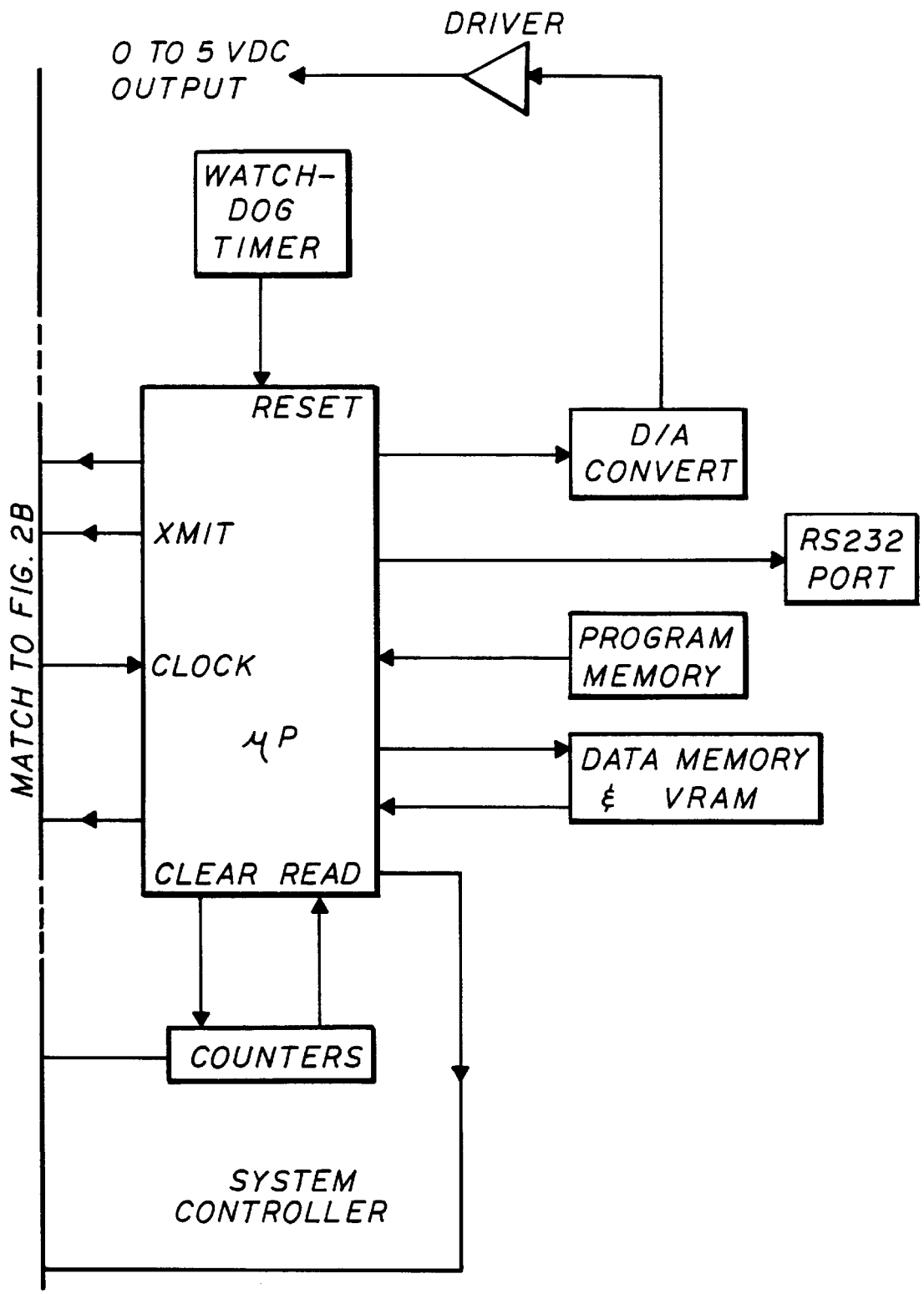

With reference next to FIGS. 2A, 2B and 2C (hereinafter collectively referred to as FIG. 2), a functional block diagram is provided of a suitable fuel gauging system that embodies the teachings of the present invention. Those skilled in the art will readily appreciate that the invention can be practiced with many different circuit configurations, and that in particular the circuitry that embodies the basic functions of the invention can be added to conventional fuel gauging systems and control circuits used with such systems. Examples given herein of types of circuits that can conveniently be used to realize the functional blocks are intended to be illustrative and should not be construed in a limiting sense. The functional blocks can be realized in many different ways in both analog and digital formats.

In the ultrasonic fuel gauging system (UFGS) of FIG. 2, the UFGS 10 includes several main functional sections. These include a controller section 12, a signal conditioning section 14 and a multiplexing section 16. This description of the circuit as having three main functional sections has no particular significance, but rather is simply used for ease of explanation and clarity. Those skilled in the art will readily appreciate that the main circuit sections are interconnected and that, in many cases, components associated with a particular section in this description could just as easily be associated or described with reference to a different section. The sectional approach is used herein because the present invention can generally be viewed as embodied in circuitry associated with the signal conditioning circuit in terms of modifications that are suitable, for example, with conventional UFGS systems, along with appropriate software changes to implement the described functions. However, the embodiment of the invention illustrated in FIG. 2 should not be construed in a limiting sense because the implementation of an echo envelope energy detection process can be realized in varied ways.

The controller section 12 includes a main CPU or microprocessor 20. Conventional devices such as 8OC31BH available from Intel Corp. can be used. The speed and control power needed from the CPU 20 will be determined in part, of course, by how many sensors are to be interrogated and how frequently data will be collected. These requirements will vary with each application, but in most cases the basic device identified herein will be suitable. The controller 20 can be programmed in a conventional manner as described in the manufacturer's specification, as is well known to those skilled in the art. The functions carried out by the software in order to realize the present invention are included in the functional flow chart in FIGS. 3A, 3B and 3C which will be described later herein.

The controller 20 operates from a main clock provided from a crystal oscillator 22, in combination with an operating program stored in a non-volatile program memory 24. The crystal oscillator 22 also provides a clock input to echo counters 26 through an enable logic gate 28. The oscillator 22 also provides a clock input to a frequency divide and select circuit 30. The frequency divide and select circuit 30 functions in a conventional manner to divide down the oscillator frequency to a frequency for operation of the ultrasonic transducers. For example, the transducers may operate at a frequency of 1 megahertz. A burst length control signal (BURST) 32 (for convenience, signals and signal lines are treated herein as one in the same—no separate reference numeral is used in the drawings to distinguish a signal from the conductor that carries that signal) from the microprocessor 20 can be used to adjust the transmit frequency based on such factors as temperature of the liquid and anticipated target range. For example, a longer transmit burst is typically used for farther target ranges (high liquid levels) while shorter bursts are typically used for shallow targets. The burst length control signal from the microprocessor 20 can thus be used to dynamically change the burst duration for each transducer.

It should be noted at this time that the embodiment illustrated in FIG. 2 shows only one ultrasonic sensor. It is very common, however, to use a large number of sensors, particularly in cases where the fluid container has an irregular configuration or when high accuracy is required, for example. The system of FIG. 2, of course, is designed to accommodate a large number of sensors, such as, for example, by time multiplexing. Thus, it is useful in most cases to provide the controller 20 with the capability to adjust the burst duration (and frequency) depending on which transducer is being activated during a particular cycle.

At the beginning of each transmit cycle, the microprocessor sends a transmit (XMIT) signal 34 that serves as a trigger signal to a blanking circuit 36, a variable pulse generator circuit 38, and a counter latch 40. The blanking circuit 36 produces an inhibit signal that disables operation of an echo amplifier 42 for a period of time following the transmit burst. This operation prevents the amplifier from saturating due to ultrasonic energy received during transducer ringing and backscatter. The amount of time delay will be determined by the burst length. Thus, the blanking circuit 36 receives an input control signal 44 from the data select circuit 30, which control signal sets the blanking time duration. The blanking circuit 36 can be conveniently realized, for example, in the form of a one-shot having a controllable variable pulse width.

The XMIT signal also triggers the variable burst circuit 38. This circuit can also conveniently be realized in the form of a variable pulse width one-shot. The circuit 38 effectively enables a gate 46 that passes the high frequency burst signal from the frequency divide circuit 30 through to a filter/amplifier circuit 48 for a period of time determined by the duration of the signal from the variable burst circuit 38.

The XMIT signal 34 also triggers the counter latch 40. In this case, the counter latch is conveniently realized in the form of an R-S flip flop that is set by the XMIT pulse and reset by a signal generated by the first return echo after blanking. The latch 40 output is used as an enable signal for the oscillator clock 22 pulses to the counters 26. Thus, the counters are enabled at the beginning of the XMIT pulse (i.e. the beginning of a transmit/receive cycle) and count the time delay until receipt of the first echo following the blanking time. The microprocessor reads the counter 26 data 50 and clears the counters after each cycle via a clear signal 52 (those skilled in the art will appreciate that the counters can in fact be a single counter or several counters chained together.)

The high frequency burst signal is filtered and amplified as appropriate by the filter circuit 48 and then connected to the transducer T or transducers for the current transmit cycle via a demultiplexer (DMUX) circuit 54. The DMUX circuit is basically an addressable switching circuit that connects the drive signal to the selected transducer T. The demultiplexer circuit receives address commands from the microprocessor in a conventional manner and decodes the addresses so that the drive signal is input to the correct transducer for the current transmit/receive cycle. A transmit/receive switch 56 under control of the microprocessor may be provided between the transducer and the demultiplexer to isolate inactive transducers from noise during each transmit/receive cycle.

When echoes are received at the transducer T, the transducer converts the acoustic energy into corresponding electrical signals and sends the echo signals to the echo amplifier 42 via a multiplexing circuit 58. The multiplexing circuit 58 operates similarly to the DMUX circuit 54 in that it is an addressable switching device that connects a selected transducer(s) output to the echo amplifier. (Note that in FIG. 2 the address control lines from the microprocessor to the MUX and DMUX circuits are not shown for clarity and convenience.) The amplified echo output from the amplifier 42 is then rectified by a rectifier circuit 60. In operation, the amplifier 42 and rectifier 60 together convert the high frequency acoustic echo signals, such as signal EC in FIG. 1A, into a dc variable echo envelope, such as the signal EC' in FIG. 1B, in effect demodulating the amplitude modulated high frequency echo signal. As previously stated, during each transmit/receive cycle the echo profile typically will contain a number of echoes, one of which is the true echo and false echoes. All of the echoes in an echo profile of a transmit/receive cycle are demodulated by the amplifier 42 and rectifier 60.

The analog echo envelope profile is input to a flash analog-to-digital converter (A/D) 62 that digitizes the echo profile at a preferably high sampling rate, for example, twice the burst frequency of the ultrasonic pulses. The rising edge of the first echo envelope is also used to trigger a level detector 64 which produces a trigger output that resets the echo latch 40 thereby disabling the counters 26. The counters 26 thus count the elapsed time between start of the transmit pulse and detection of the first echo that exceeds the threshold of the detector 64.

The digitized echo profile for the transmit/receive cycle is then stored in a temporal manner in a memory device 66 which may conveniently be realized in the form of a dual port RAM controlled by the microprocessor 20. Thus the data position in the memory 66 corresponds to the time of detection of the echo. Data can be written through one port of the memory on data lines 68, and read out by the microprocessor 20 on data lines 70. This configuration permits very fast access to the echo profile by the microprocessor. Under instruction of the main program in memory 24, the microprocessor then determines the true echo and the round trip time to receipt of that echo as an indication of fluid level above the transducer that produced the particular echo profile analyzed. This data can then be stored by the microprocessor in a data memory device 72, which may include a video memory for visual display of the data. The microprocessor may also send the data to a peripheral device or other controller via a serial port 74. The microprocessor 20 can also be programmed in a conventional manner to adjust the gain of the amplifier 42 as a function of the expected range of the true target, since echo strength decays as the target distance increases. Gain adjustment can be controlled, for example, by a standard automatic gain control circuit (AGC) 76.

In the specific embodiment of FIG. 2, the first echo received back after the blanking period is initially assumed to be the true echo. This is typically the case, for example, in fuel level sensing systems. Thus, the counters 26 are triggered in response to the first echo. However, as explained hereinbefore, false echoes can be received such as due to air bubbles or fuel/water interfaces. In such circumstances, the first echo back after blanking may not be the true echo. In accordance with the invention, the microprocessor is configured to determine the echo energy for echo envelopes that exhibit maximum peak amplitudes during a transmit/receive cycle. The microprocessor further determines which echo has the maximum energy. When the maximum energy echo has been identified, its temporal location can be determined. If the maximum energy echo occurred at the same time as the first echo that disabled the echo counters 26, then the first echo is confirmed as the true echo. If the maximum echo energy occurred at a different time than the first echo, then the maximum energy echo is considered to be the true echo. The false echo resolution of the first echo can also be confirmed by determining the energy content of the first echo and verifying that the energy level is too low for a true echo from the fluid surface. Further verification can be accomplished by using a time domain window after a true echo position has been determined. In other words, once a true echo is identified, subsequent true echoes can be expected to occur within a specific time window around the previous echo.

In cases where the first echo is typically the true echo, the verification process can be performed at a slower rate that every transmit/receive cycle. For example, the echo energy determination can be performed every five transmit/receive cycles, or at some other suitable interval.

Figure 3A:
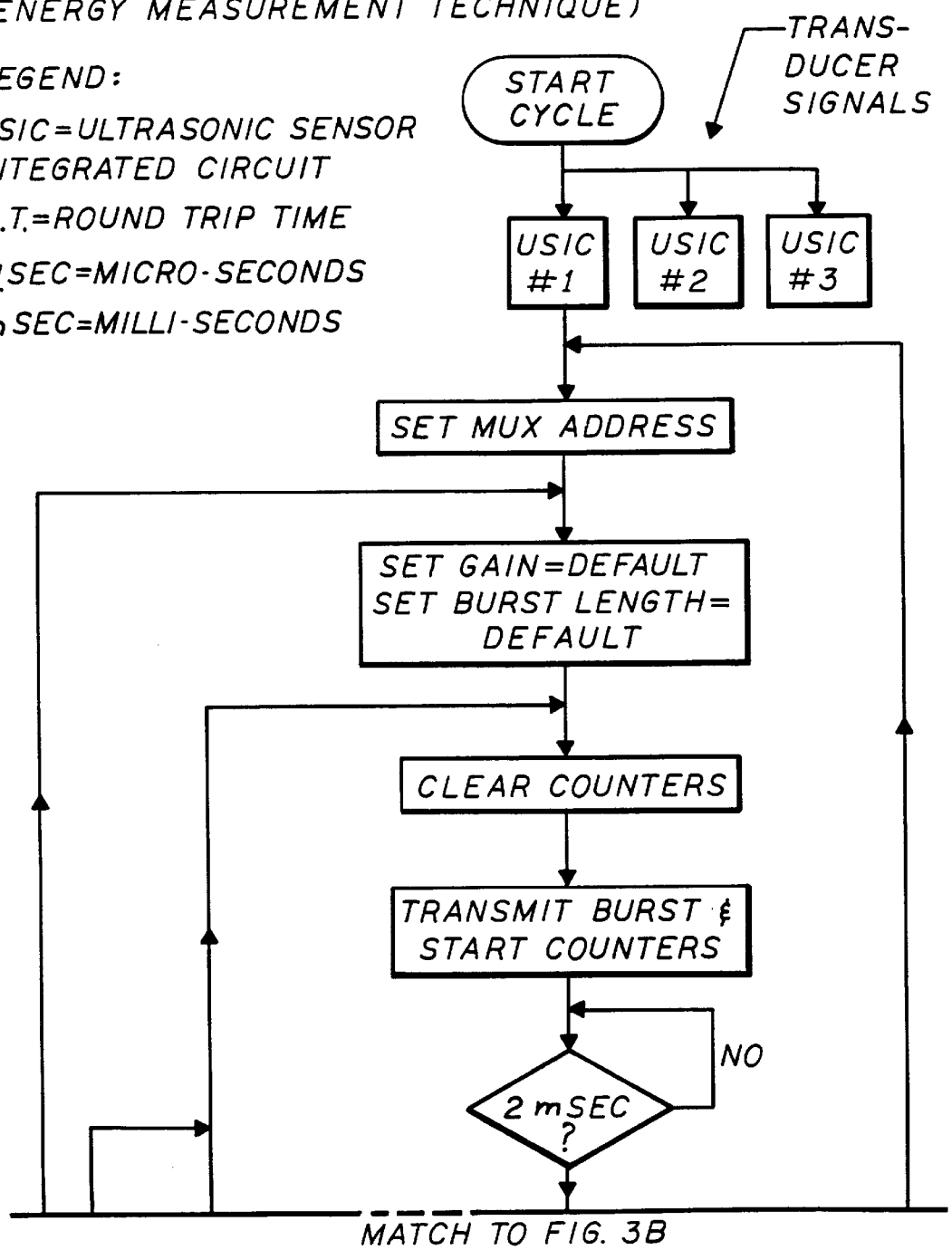
FIGS. 3A, 3B and 3C is an flow chart for the operational sequence and control functions of the fuel gauging system shown in FIGS. 2A, 3B and 2C according to the invention.
Figure 3B:
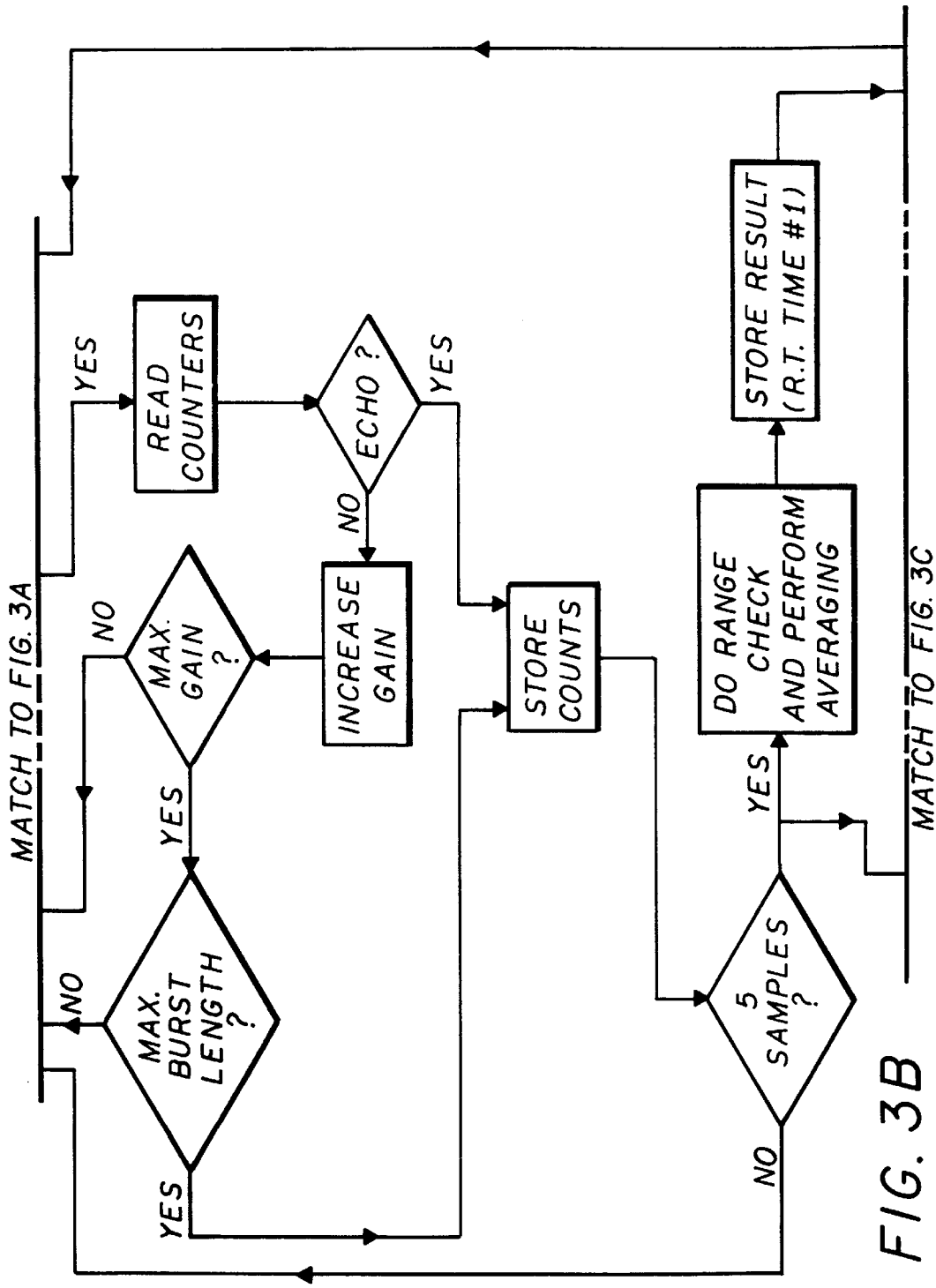
Figure 3C:
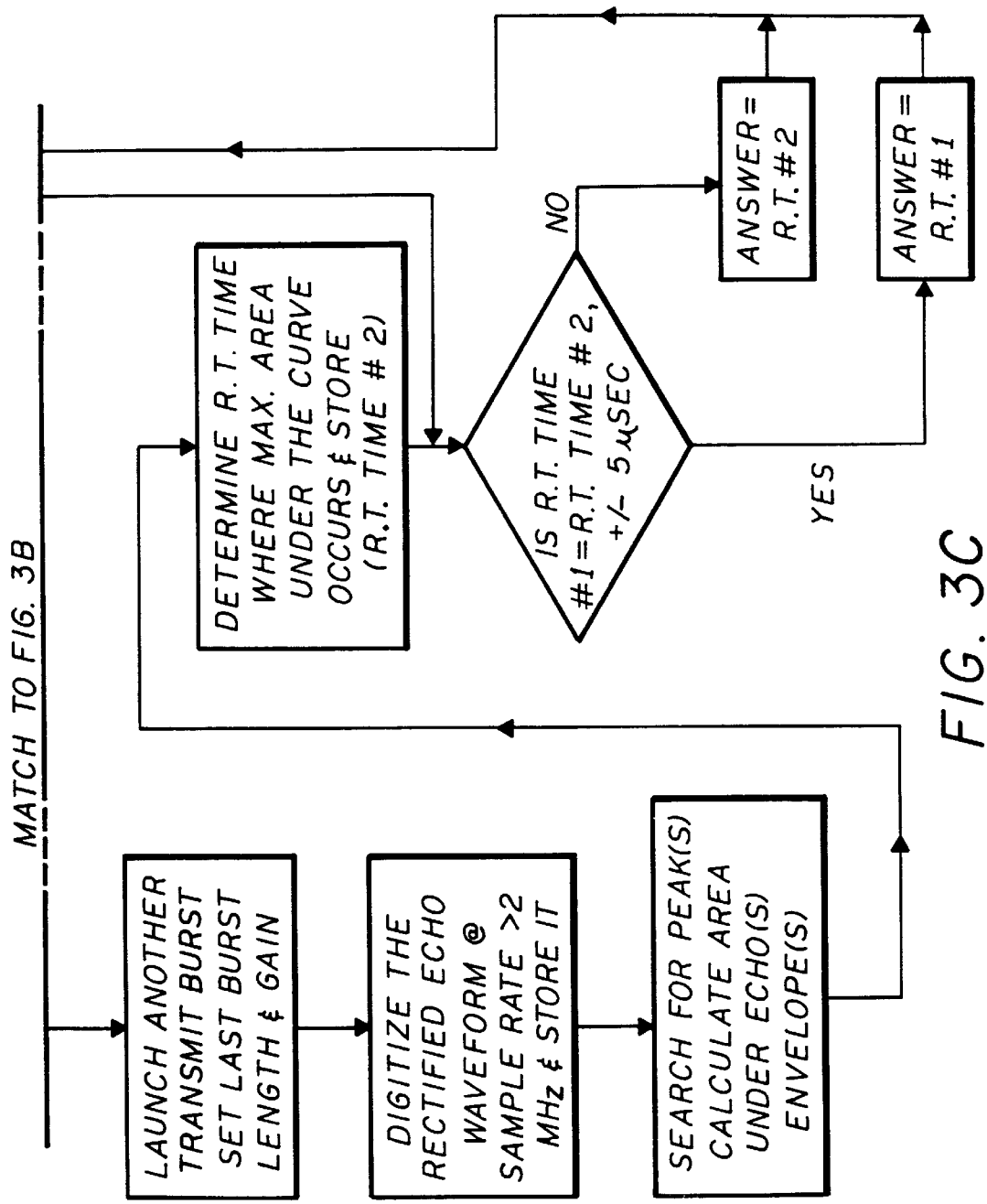

With reference to FIGS. 3A, 3B and 3C (hereinafter collectively referred to as FIG. 3), a suitable control sequence for the microprocessor 20 is shown in a flow diagram. In this case, the echo energy determination is made every five transmit/receive cycles.

At step 100 a transmit/receive cycle is initiated and one or more transducers are selected through the multiplexer switch (102). In the example of FIG. 3, transducer #1 is selected for the described cycle. If the current cycle is the first cycle, then at 104 the transmit burst length and echo amplifier gain are set at default values determined by expected echo characteristics.

At step 106 the echo counters 26 are cleared or reset and at step 108 the transmit pulse is sent and the counters are enabled and the blanking pulse is generated. A maximum range clock is used to determine at step 110 whether a maximum time period has elapsed after which no valid echo could be received. After the maximum echo range period expires, for example 2 milliseconds, the counters 26 are read at step 112. If the counters read less than 2 milliseconds then the controller 20 knows that an echo was detected. If no echo was detected the controller branches at 115 to steps 114, 116 and 118 and then back to step 106 for a new transmit pulse. Steps 114, 116 and 118 are used to incrementally increase the transmit burst length and/or gain of the echo amplifier 42 until an echo is detected as indicated by the state of the counters 26.

After an echo is detected, the controller stores the echo count in memory at step 120. Note that step 120 is also reached if no echo is received after maximum gain and burst length have been attempted.

At step 122 the controller determines if, in this case, five transmit/receive cycles have been completed, either with five echoes detected or some number of echoes less than five detected and the balance including the counter value for max burst and gain attempts. After five samples have been stored in memory, at step 124 the controller calculates the average range for the five detected echoes (range being a function of the counter time measurements.) Keep in mind that at this point the five samples are for the first detected echo after the blanking period. These first five echoes are not necessarily known or verified to be true echoes yet. At step 126 the controller 20 stores the average range in a memory location.

In addition to performing the averaging function after five samples are received, the microprocessor 20 at step 128 commands another transmit burst at the last burst length and gain value known to have produced an echo detection. The entire echo profile received over this verification transmit/ receive cycle period is stored in the dual port memory 66 at step 130. At step 132 the microprocessor 20 scans the stored echo profile and locates the echo peaks among the various echo envelopes. After determining the higher peak echoes, the system calculates the energy of each of the high peak echoes. In this case, echo energy is calculated by adding the echo amplitude values for a plurality of time intervals around the time that the echo peak occurred. This process is facilitated in the described embodiment because the digi-tized data directly corresponds echo amplitudes with discrete time intervals in the echo envelope. For example, if an echo peak is detected at 200 microseconds, echo amplitude values at one microsecond intervals, for example, on either side of the 200 microsecond peak are added together. The samples are added until the echo amplitudes fall below a selected threshold level. This total then corresponds to the total energy of the echo. This process is repeated for each echo envelope that exhibits a peak amplitude above a selectable threshold.

The echo exhibiting the maximum energy or area under the envelope curve (see FIG. 1B, for example) is identified as a true echo, and at step 134 the microprocessor determines the time at which the true echo was received. At step 136 the time occurrence of the maximum energy echo is compared with the time occurrence of the average first echo that was detected at step 126. If the two time events correspond, then the microprocessor accepts the first echo as a true echo (step 138.) If the two time events do not correlate, then the microprocessor accepts the maximum energy echo as the true echo(step 140.) The system then returns to the start of the process and interrogates the next transducer sensor(s) in the system array.

The invention thus provides an ultrasonic liquid level sensing system that uses an improved echo discrimination technique to separate true echoes from the liquid surface from false echoes such as are produced by air bubbles and non-surface interfaces, such as a water/fuel interface in a fuel tank. The echo discrimination technique is based on determination of echo energy, which produces a more reliable and accurate discrimination than amplitude based or pulse width based techniques that rely on time variable thresholds.

Although the described embodiment of the invention includes a blanking period to force the system to ignore the transducer ringing and backscatter after transmit, the system could be operated to receive the entire post-transmit echo profile (other useful information can in some cases be extracted from the initial echo.) In such a case, the system would ignore the initial echo data in searching for the maximum energy echo and would trigger the counters 26 as a function of the second received echo. Also, while the described embodiment uses digital conversion and storage of the echo profiles to facilitate echo energy determination, echo energy could also be determined in an analog fashion, such as, for example, with the use of CCD arrays that can store analog signals.

While the invention has been shown and described with respect to specific embodiments thereof, this is for the purpose of illustration rather than limitation, and other variations and modifications of the specific embodiments herein shown and described will be apparent to those skilled in the art within the intended spirit and scope of the invention as set forth in the appended claims.

What is claimed is:

1. A method for discriminating true and false echoes in an ultrasonic liquid gauging system comprising the steps of:
   a. transmitting an ultrasonic pulse toward the liquid surface;
   b. detecting true and false echoes after a transmission; and
   c. identifying a true echo from a false echo based on energy of the echoes by determining which echo has the higher energy.

2. The method according to claim 1 wherein said step of identifying a true from a false echo comprises the steps of detecting peak amplitudes of the echoes, identifying which echoes have higher peak amplitudes relative to the detected echoes, and calculating the energy, in each of said peak amplitude echoes.

3. The method according to claim 2 wherein the step of calculating the energy in each of said peak amplitude echoes comprises the step of summing a series of amplitude values of an envelope of each echo for discrete time intervals around the amplitude peak time.

4. The method according to claim 3 further comprising the step of using a counter to determine when a second echo after transmission is received.

5. The method according to claim 4 wherein said energy detection is used as a verification that the second echo received is a true echo.

6. The method according to claim 5 wherein said counter timing is performed for the second received echo each transmission cycle, and said energy detection is performed periodically at a rate slower than every transmission cycle.

7. The method according to claim 6 further comprising the step of storing the electrical echo signals in a memory device and includes the step of digitizing the entire echo profile for selected transmit/receive cycles.

8. Apparatus for discriminating true echoes from false echoes in an ultrasonic liquid gauging system, comprising: means for producing electrical representations of an echo sequence received after an ultrasonic transmission, wherein the echo sequence contains one or more returned echoes that may be a true or false echo; and means for determining returned echo energy, wherein a true echo is distinguished from a false echo by determining which echo has the higher energy.

9. The apparatus of claim 8 wherein said energy determining means comprises control means that calculates energy of returned echoes that are possible true echoes based on peak amplitude determinations of the returned echoes.

10. The apparatus of claim 9 wherein said control means comprises a counter that determines the elapsed time from transmission to detection of a second returned echo.

11. The apparatus of claim 10 wherein said control means averages the elapsed time measurements of detecting the second returned echo for a plurality of transmission cycles.

12. The apparatus of claim 11 wherein said control means determines the returned echo that is a possible true echo and has the highest returned energy, and determines the elapsed time to detection of said echo; said energy determination of a true echo being used by said control means to verify that the second returned echo is a true echo.

13. The apparatus of claim 12 wherein said control means selects the true echo based on said energy determination over the second returned echo if the energy determination fails to verify that the second return echo is not a true echo.

14. The apparatus of claim 13 wherein said means for producing electrical representations comprises memory means for storing electrical signals that correspond in time and amplitude to echo pulses in an echo sequence.

15. The apparatus of claim 14 wherein said memory means stores echo sequences in a temporal manner such that said control means can determine elapsed time between a transmission event and detection of the returned echoes.

16. The apparatus of claim 15 wherein said control means determines echo energy by adding amplitude values at discrete time intervals around the time occurrence of an echo peak amplitude.

17. The apparatus of claim 16 wherein said memory means comprises a flash A/D converter that receives analog returned echo amplitude signals, and an electronic memory device that sequentially stores digitized values of returned echo amplitudes produced by said A/D converter.

18. The apparatus of claim 17 comprising a plurality of ultrasonic transmission devices, said control means interrogating each sensor in a time multiplexed manner.

19. The apparatus of claim 18 in combination with a liquid gauging system comprising a plurality of ultrasonic transducers used to emit ultrasonic pulses towards the surface of a liquid held in a container.

20. The combination of claim 19 wherein said liquid gauging system is an ultrasonic fuel gauging system for aircraft fuel tanks.

* * * * *